United States Patent [19]

Christlieb

[11] Patent Number: 5,158,097

[45] Date of Patent: Oct. 27, 1992

[54] PARANEURAL STIMULATING LEAD

[75] Inventor: Ignacio Y. Christlieb, Pittsburgh, Pa.

[73] Assignee: Allegheny-Singer Research Institute, Pittsburgh, Pa.

[21] Appl. No.: 534,760

[22] Filed: Jun. 8, 1990

[51] Int. Cl.⁵ .............................................. A61N 1/05
[52] U.S. Cl. .................................. 128/785; 128/642; 128/784; 128/786
[58] Field of Search ........... 128/783, 784, 786, 419 R, 128/419 P, 639, 642, 785

[56] References Cited

U.S. PATENT DOCUMENTS

| Re. 26,809 | 3/1970 | Hagfors | 128/784 |
| Re. 26,810 | 3/1970 | Schwartz et al. | 128/784 |
| 1,056,336 | 3/1913 | Hurdman | 128/786 |
| 4,325,389 | 4/1982 | Gold | 128/784 |
| 4,677,989 | 7/1987 | Robblee | 128/784 |
| 4,791,911 | 12/1988 | Magovern | 623/3 |
| 4,800,898 | 1/1989 | Hess et al. | 128/786 |

Primary Examiner—William E. Kamm
Assistant Examiner—Kennedy J. Schaetzle
Attorney, Agent, or Firm—Webb, Burden, Ziesenheim & Webb

[57] ABSTRACT

This invention pertains generally to an implantable medical lead for stimulating muscle or tissue contraction and a method for using the same, and specifically to a paraneural electro-stimulating bipolar shielded lead and a method for using the same, for use in surgical procedures such as the Muscle Flap Heart Function Augmentation Procedure and/or other circulatory augmentation procedures, and/or wherever stimulation of muscle or tissue is desired.

14 Claims, 4 Drawing Sheets

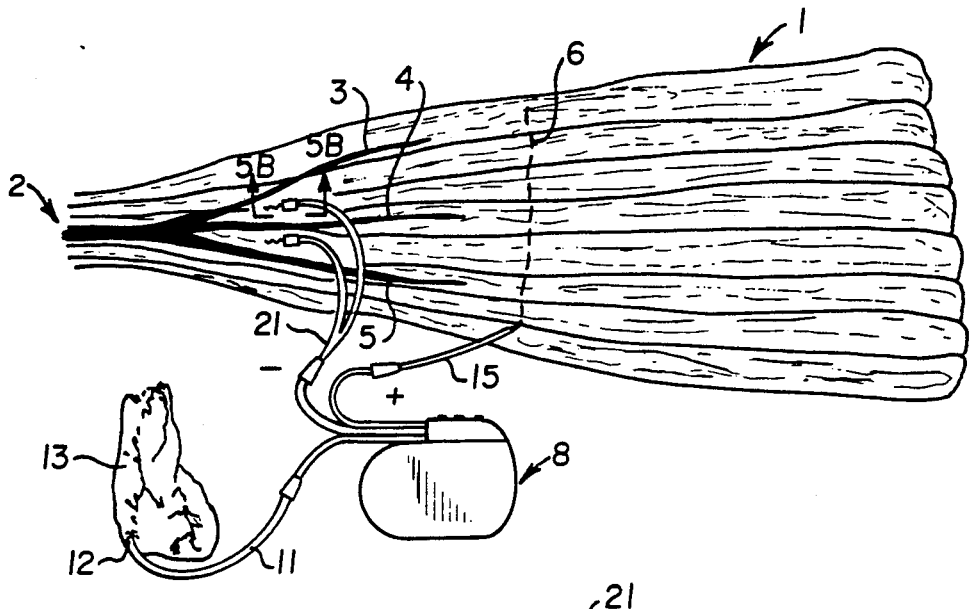
FIG. 5A PRIOR ART
FIG. 5B PRIOR ART
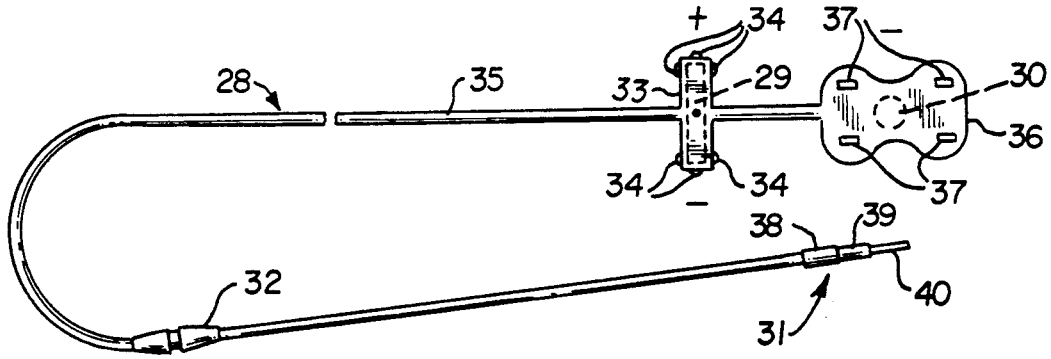
FIG. 6A
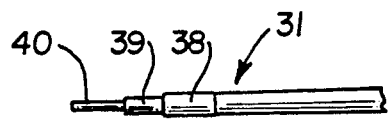
FIG. 6B

PARANEURAL STIMULATING LEAD

BACKGROUND OF THE INVENTION

1. Field of the Invention

This invention pertains generally to an implantable medical lead for stimulating muscle contraction, and specifically to a paraneural electrostimulating bipolar shielded lead for use in surgical procedures such as the Muscle Flap Heart Function Augmentation Procedure and/or other circulatory augmentation procedures powered by skeletal muscles.

2. Description of the Prior Art

Congestive heart failure represents a pathophysiologic state in which cardiac output is inadequate to meet the demands of a body. Reduced cardiac output results from many known conditions and diseases, including ventricular tumors and/or aneurisms, stenosis or other diseases of the valves, cardiac muscle damage due to myocardial infarction, toxic or inflammatory diseases, and the like. Cardiac transplantation and the mechanical heart are among the most recently developed invasive methods of improving cardiac output. While clinical results with cardiac transplantation have been impressive, progressive cardiac deterioration frequently results from localized cardiac muscle damage which, at least in theory, would not terminate requiring cardiac transplantation if alternative methods of cardiac assistance and/or reconstruction were available. Further, the limited availability of matching or compatible donor organs significantly restrains the number of patients who can benefit from this procedure. Mechanical circulatory support devices have been used to assist failing ventricles, to serve as a bridge for cardiac transplantation, and to provide limited-term circulatory support. However, the complex mechanisms of power supply, the prohibitive costs, and the complications of thromboembolism and infection have limited the success of the mechanical heart.

Just as prostheses were developed to repair damaged or diseased cardiac valves, similarly, a significant need persists for a method of reconstructing and/or supplementing cardiac muscle in the event of localized damage such as ventricular tumor or aneurism or some forms of global abnormality.

In order to meet this need, a surgical procedure known as Muscle Flap Heart Function Augmentation which is capable of increasing cardiac output was pioneered by George Magovern, M.D. This procedure is also known as cardiomyoplasty and is disclosed and claimed in U.S. Pat. No. 4,791,911 issued Dec. 20, 1988 to George Magovern, M.D.

This surgical procedure utilizes the principle that both cardiac and skeletal muscle are composed mainly of contractile proteins that can transform chemical energy into mechanical work. The myocardium is by nature a highly fatigue resistant and oxidative metabolizing muscle that is capable of continuously pumping blood for a lifetime. It has been found that with proper training through electric conditioning, skeletal muscle fibers can be transformed so that they function like those of the myocardium.

In the cardiomyoplasty surgical procedure, a patient's either (or both) latissimus dorsi muscle(s) is (are) dissected from its (their) natural location in the back. The blood supply and nerve tissues are not divided and remain intact to nourish and excite the muscle. The dissected muscle (also known as and hereinafter referred to as the "muscle flap") is translocated by passing it into the thorax through a partial rib resection below the axilla. After appropriate midsternotomy, cardiac surgery (and cardiopulmonary bypass when needed) etc., the muscle flap is used as a graft in the reconstruction of cardiac walls or wrapped around the ventricle(s) as a reinforcing structure.

For several days post-operatively, the muscle flap is permitted to heal in its new anatomical position before stimulating contractions (which might otherwise tear the sutures) are initiated. Subsequently, a protocol of suitable electric stimulating of the muscle flap is initiated, which enables the muscle flap to contribute to the overall cardiac function and cardiac output once the muscular fibers have been "trained" or "conditioned".

It has been found that the muscle flap can be made to beat in synchrony with the heart in response to signals generated by a type of cardiac pacemakers and/or a type of implantable pulse generator (IPG) as hereinafter described and generally known as a cardio-muscle stimulator, although it may be known by other names or terms as well. Further, as used herein, the term cardiomuscle stimulator is defined to include one or more devices, elements or any combination or configuration that is implanted for the purpose of stimulating live graft tissue to augment cardiac or circulatory function, including, but not limited to, co-pulsating and counter-pulsating devices. One example of such a device is Model SP1005, marketed under the trademark Cardio-Myostimulator ™ available from Medtronic®, Inc., of Minneapolis, Minnesota.

The cardio-muscle stimulator is both a "receiving" and a "sending" unit As the heart muscle begins its contraction, a sensor which is associated with the heart, senses the occurrence of electrical impulses generated by the heart muscle (specifically the depolarization of the atria or ventricles), which immediately precedes and initiates systolic contraction. The sensor in turn transmits a signal which is "received" by the cardio-muscle stimulator. The cardio-muscle stimulator in turn transfers that signal to its "sending" unit portion. The muscle channel, or sending unit portion of the cardio-muscle stimulator, generates stimulating pulses individually, or in a burst pattern, and—through a combination of stimulating leads which include electrodes implanted in the muscle flap—causes the muscle flap to contract in synchrony with the heart to which it is attached, assisting the heart and causing it to increase its output of blood to the body. The cardio-muscle stimulator is usually but not necessarily implanted in the upper left portion of the abdominal wall.

To understand the present invention, it is important to have an understanding of the association of the stimulating leads and electrodes with the muscle flap, and the process by which a signal generated by the cardio-muscle stimulator will cause a muscle flap to contract.

The latissimus dorsi of an adult is typically approximately 30-40 cm. long by 15-25 cm. wide and varies in thickness throughout its length. The general structure of such a flap is depicted in FIG. 1, and it will be helpful to review FIG. 1 before proceeding further. As depicted in FIG. 1 (discussed in greater detail, infra), the neurovascular bundle, in this case, the thoracodorsal bundle, comprising an artery, a vein, and a nerve, enters the head of the muscle flap, and similarly to a tree trunk and several branches, the neurovascular bundle ("trunk") subsequently branches into ever smaller dimensions as it permeates the entirety of the muscle flap.

The output signal of the cardio-muscle stimulator is transferred via stimulating leads to the muscle flap by placing the electrodes of the stimulating leads in contact with the muscle flap in the vicinity of the main nerve and/or major branches.

More specifically, the current art utilizes separate positive and negative electrodes placed within approximately 6 to 12 cm. of each other in the vicinity of the main nerve and/or major branches. While a single electrode could theoretically be used, with current returning to the case of a cardio-muscle stimulator which design allows it to be an electrical current ground, the use of two electrodes (comprising a positive and a negative) is preferred because this provides an efficient path for the current to travel resulting in a more efficient stimulation of the structure of the muscle flap. In the standard two-electrode system, current travels from the cathodic to the anodic electrode.

It should be noted that the stimulation of the muscle flap proceeds via the process known as "neuromuscular distribution"—wherein some muscle fibers (along with the main nerve branches) are electrically stimulated, which in turn carry the stimulus chemically or electrochemically throughout the network of nerve branches which permeate the muscle flap, causing the fibers of the entire muscle flap to contract in response to the stimulus. This process should be distinguished from the stimulation of a single nerve branch in order to produce contractions of limited portions of muscle tissue. Further, it should be noted that the electrode portions of the stimulating leads are not placed in direct contact with the nerve, but are associated with the muscle tissue itself near the main nerve branches.

The use of medical leads is known, and certain terms common in the art connected with those leads/electrodes are generally defined and understood herein as follows:

"Unipolar" refers to leads having a single electrode, which could be either a negative (−) (cathode) or a positive (+) (anode) but not both. Typically, two unipolar electrodes (a positive electrode and a negative electrode) are required to achieve stimulation of the muscle flap;

"Bipolar" refers to leads which have both a positive (+) (anode) and a negative (−) (cathode) portion integrally formed in a single stimulating lead;

"Shielded" refers to a lead wherein the cathodic and/or anodic electrodes are in part covered with electrical insulation—permitting current to be released to or from the anode and/or cathode only in a specific limited direction, as in some limited portions of a plate, a rod or a sphere, as opposed to an unshielded electrode as defined below;

"Unshielded" when used in relation to an electrode, indicates that whether it is the anode and/or cathode, it is not covered by electrical insulation over any portion of its surface and may therefore release current in any and/or all directions along the exposed plate, rod or sphere. It is to be understood that "over any portion of its surface" means that portion of the electrode in contact with nerve or muscle tissue, it is being further understood that the portion of the lead not in contact with live tissue may be electrically insulated ("shielded") to prevent undesirable stimulation of structures located between the cardio-muscle stimulator and the muscle flap;

"Electrode" means the potentially active, non-electrically insulated portion of a lead and is further used as a general term which can mean either an anode and/or a cathode;

"Stimulating lead" refers to a lead which conducts electric stimuli from a power source to the receiving tissue, and incorporates all components of the lead from the point of attachment to a stimulating power source to its distal end, including the electrode(s). The stimulating lead may be used as a pacing lead;

"Pacing lead" refers to a lead which is similar in design to a stimulating lead except that the purpose of the pacing lead is usually directed to cardiac pacing.

It is to be noted that while the terms "pacing lead" and "stimulating lead" are nearly identical, and in fact are often used interchangeably in the art historically the term "pacing" has evolved in connection with the rhythmic pacing of cardiac tissue. While the pacing of cardiac tissue and the stimulation of non-cardiac muscle share some areas of technical overlap, there are also very significant technical differences associated with each of these procedures, therefore, the term "pacing" will more correctly identify the stimulation of cardiac tissue, whereas the term "stimulating" will more correctly identify the stimulation of non-cardiac tissue, specifically of skeletal muscle, which is being used to augment cardiac or circulatory function.

Additionally, there are several types of leads which lend themselves to various means of attachment to body tissue, which include the following:

"Screw-in" or "corkscrew lead" refers to electrodes having a screw or spiral-type configuration which is screwed into the tissue;

"Stab-in lead" refers to the method of electrode attachment wherein the electrode is positioned over the cardiac or skeletal muscle tissue and is implanted therewith by utilization of point and barb system similar to that of a fishing hook;

As used in conjunction with the concept of electrode attachment to body tissue, "suture lead" refers to a means of attaching the lead to body tissue and the lead is equipped with points of attachment which permit the electrode to be fixed with stitches to the tissue;

"Tined lead" refers to a lead with one or more tined portions, similar to a grappling hook, which is capable of affixing itself to the tissue in the same manner as a grappling hook attaches to various items as distinguished from the point and barb method of attachment of the stab-in type method of attachment;

"Wrap-around lead" refers to a lead which is physically wrapped around the tissue to be stimulated (which may be unipolar or bipolar in configuration);

"Intramuscular lead" refers to a lead which can be routed through the muscle flap tissue.

A) Specific Combinations/Specific Tasks

Of the above-listed electrode or lead configurations and methods of attachment, certain combinations are most commonly used for specific applications.

For example, cardiac pacing typically utilizes either an "epicardial" pacing lead (which is fastened externally to the heart muscle) or an "endocardial" pacing lead (which is inserted through a vein leading to the heart and then subsequently advanced into the interior of the heart). Neural stimulation typically utilizes a wrap-around stimulating lead. Each of these leads generally has the following standard configuration.

1. Epicardial Pacing Leads and Electrodes—Unipolar/Shielded

The standard epicardial pacing lead used in the art (which is attached to the external surface of the heart) utilizes a unipolar/shielded electrode which is typically attached with a stab-in or a screw-in type method of attachment to the heart.

2. Endocardial Pacing Leads and Electrodes—Bipolar/Unshielded

The endocardial pacing lead is typically bipolar with two unshielded electrodes which, as indicated, is inserted directly into the interior of the heart wherein it attaches itself with a screw-in or tined type method of attachment. Particular note should be taken of the fact that the cathode is located at the most distal point of the endocardial lead, in a generally vertical plane perpendicular to the lead body, to insure contact of the tip of the lead with the internal surfaces of the right cardiac ventricle as the lead is pushed in a forward direction into the interior of the heart.

3. Neural Stimulating Leads—Bipolar/Shielded

Neural stimulating leads known in the art, are generally used as pain blocking devices. These neural stimulating leads typically use bipolar/shielded electrodes mounted in a sleeve or a cuff-like mechanism which is wrapped around a single nerve. Such neural stimulating leads require the nerve to be dissected and separated from any surrounding tissues such that the sleeve or cuff-like mechanism may be wrapped around and attached to the nerve. This type of lead suffers from the limitations that: 1) it requires the nerve to be separated from its surrounding structures which increases the danger of damaging the nerve or the surrounding structures during surgical operations; and 2) the proper placement and attachment of the sleeve or cuff-like mechanism around the dissected nerve is quite difficult and will damage the nerve if the sleeve or cuff-like mechanism is either too loose or too tight.

B) Current Cardiomyoplasty Leads

Two types of stimulating leads have typically been used in the cardiomyoplasty procedure. These are known as the "intramuscular" lead or electrode and the "dual screw-in type" lead or electrode. While the terms "lead" and "electrode" are often used interchangeably in the art, for consistency, the term "electrode" will be used hereinafter to refer to the anode and/or cathode and the term "lead" will refer to all components, including the anode and/or cathode.

1. Intramuscular Stimulating Lead—Unipolar/Unshielded

The intramuscular stimulating lead (an example of which is Medtronic ® Model SP5528) utilizes a unipolar/unshielded flexible coil wire electrode made of platinum-iridium and a moveable polyurethane insulating sheath. The distal part of the electrode ends in a tip that holds a non-absorbable suture filament with a curved needle for lead insertion into the muscular tissue of the muscle flap and for stable positioning. Typically, the curved needle is threaded through the muscular tissue in a sigma-like or sino-wave-like routing, pulling the suture filament in its wake, and in turn, the electrode itself. This results in increased electrode contact and reduction of mechanical stress induced by the muscular contractions. After threading the electrode through the entire width of the muscle flap as described, the suture filament is fastened on the side of the muscle flap opposite from the entry of the needle, the excess suture filament is cut off, and the moveable polyurethane sheath is moved forward until its distal end reaches the entrance side of the lead into the muscle flap whereupon the polyurethane sheath is also then secured to the muscle flap, leaving no unshielded electrode surface outside the muscle flap (although the electrode itself inside the muscle tissue is completely unshielded).

The major limitation with the use of the intramuscular stimulating lead is that the process of insertion (particularly since insertion occurs near the point of entry of the neurovascular bundle into the latissimus dorsi) has the potential to damage by accidental penetration or severing, both the blood vessels and the nerve trunk or branches which nourish the muscle flap, whereupon the muscle flap will be rendered useless for the purpose of the cardiomyoplasty procedure. Further limitations include that the insertion of the intramuscular electrode can be difficult and time consuming under operating conditions. Further, as the intramuscular electrode is a unipolar/unshielded electrode, two such electrodes must be inserted into the muscle flap in order to have the necessary bipolar system for the dynamic cardiomyoplasty procedure, thus doubling the risks associated with the use of the single bipolar lead.

2. Dual Screw-in Type Stimulating Leads—Unipolar/Unshielded

Additionally, dual screw-in type stimulating leads have been utilized with the cardiomyoplasty procedure. These leads have unipolar/unshielded electrodes. What is meant by "dual" is that instead of utilizing a single unipolar/unshielded screw-in type lead (for use as the cathode, for example) the "dual" screw-in type muscular lead (an example of which is Model SP5537 from Medtronic ®) splits the cathode into two parts, each part having a screw-in lead at its distal tip. Thus, a typical dual screw-in type lead anode/cathode system will consist of four individual electrodes, two cathodes and two anodes.

With the use of an insertion tool, the dual screw-in type lead is placed between each pair of the three main nerve branches of the nerve trunk of the muscle flap near the head of the muscle flap at approximately 45 degrees with the muscle flap surface. The reasons for using dual electrodes include: 1) to ensure a more complete fiber recruitment; and 2) to allow for redundancy. In one embodiment of the Muscle Flap Heart Function Augmentation Procedure as described above, a dual screw-in type lead is used as the cathode, whereas the intramuscular lead previously discussed above, is used as the anode.

Limitations of this unipolar/unshielded screw-in type lead include: 1) that two electrodes are needed for each lead. This means that there are two points of contact into the muscle tissue per lead with twice the possibility of damaging the neurovascular bundle at any of the branches near the head of the muscle flap; 2) the possibility of dislodgment of the inserted electrodes; and 3) the increased difficulty of routing of the wires attached to each electrode back to the generating portion of the cardio-muscle stimulator. This type of lead did not become commercially available and has been eliminated from present day cardiomyoplasty.

Both the dual screw-in type lead and the intramuscular lead systems typically utilize a "dual barrel" or "y" connector to unite the separate positive and negative leads in a single bipolar lead connector to fit the "muscular port" of the cardio-muscle stimulator. This connector greatly increases the possibility of complications by means of its bulkiness and by adding two "set screw" connections per system, which are areas known for possible electrical disturbances.

Thus, there remains a need in the art for a stimulating lead for use with the cardiomyoplasty surgical procedure which is easily attached to the muscle flap, which minimizes the possibility of damage to the neurovascular bundle, which is capable of efficient stimulation of the muscle flap via neural distribution, which utilizes less power to do so, thereby prolonging the battery life of the cardio-muscle stimulator and which involves less foreign material to be implanted and less connections to be made.

SUMMARY OF THE INVENTION

The present invention, a paraneural lead, overcomes the above-described limitations by providing electrical stimulation to the nerves in a paraneural fashion. The lead is easily attached to the muscle flap so that damage to the neurovascular bundle is less likely to occur. It efficiently stimulates the muscle flap by way of neural distribution so that fewer electrodes are needed to provide stimulation. Using fewer electrodes reduces the likelihood of malfunction and infection.

The term "paraneural" is formed from the Greek prefix "para"—meaning "beside, beyond, accessory to, apart from, against, etc..." and "neural" (Latin neural; Greek: neuron) pertaining to a nerve or nerves, to denote an electrode or lead that is used beside, near or alongside a nerve to cause stimulation of the nerve.

The present invention also provides a paraneural lead which is capable of stimulating the nerve of the muscle flap but does not require an electrode to be in direct contact with the neurovascular bundle.

The present invention also provides a paraneural electrode which uses a bipolar/shielded electrode system utilizing a single lead body which is capable of fixation to the muscle tissue of the muscle flap away from the nerve trunk or its branches.

Additionally, the present invention provides a paraneural lead which provides for controlled unidirectional stimulation towards the nerve of the muscle flap by means of electrodes facing directly the surface where implanted and by insulating said electrodes from surrounding structures and tissues with protective shielding.

The present invention further provides a paraneural lead which permits a single flexible insulated lead which integrates a bipolar system in a single lead body. A further object of the present invention is to provide a paraneural lead which is capable of stimulation of non-cardiac or skeletal muscle by way of neural distribution.

Additionally, the present invention provides a paraneural lead having a low-energy threshold and high efficiency, which is capable of stimulating the muscle flap with less tissue damage and further providing for prolonged battery life in the stimulating device.

Finally, the present invention provides a paraneural lead having a bipolar electrode system wherein at least one of the electrodes is comprised of either a porous head to increase its surface area and/or a substance-eluting tip to lessen inflammatory tissue changes and/or can be comprised as well of carbon fiber, platinum-iridium alloy or any suitable material which provides for a less reactive, long lasting, effective conducting material.

These and other objects are attained in the present invention which provides a paraneural stimulating lead for stimulating tissue comprising:
  at least one first section comprising a bipolar, shielded lead further comprising at least one shielded anode and at least one shielded cathode;
  at least one second section comprising a connecting device for physically and electrically connecting said bipolar shielded lead to a stimulating device; and
  a third section physically and electrically connecting said first section and said second section, said third section comprising a device for conducting a stimulating current discharge generated by said stimulating device between said first section and said second section.

These and other objects are attained in the present invention which also provides a paraneural stimulating lead for use with cardiomyoplasty comprising:
  a bipolar shielded lead further comprising at least one shielded anode and at least one shielded cathode, wherein the shielding around said shielded anode and said shielded cathode restricts the direction of flow of a stimulating current discharge so that said stimulating current discharge generated by a cardio-muscle stimulator flows undirectionally into a muscle flap to which said bipolar shielded lead is attached;
  said bipolar shielded lead further comprising a connecting device capable of physically and electrically connecting said bipolar shielded lead to said cardio-muscle stimulator;
  said bipolar shielded lead further comprising a device for electrically conducting said stimulating current discharge between said connecting device and said shielded anode and said shielded cathode.

These and other objects are attained in the present invention which also provides a method of stimulating cardiac and non-cardiac tissue comprising:
  contacting a paraneural stimulating lead with tissue to be stimulated;
  connecting said paraneural stimulating lead to a stimulating device;
  inducing said stimulating device to generate a stimulating current discharge;
  transferring said stimulating current discharge to said tissue through said paraneural stimulating lead;
  wherein said paraneural stimulating lead comprises at least one first section comprising a bipolar, shielded lead further comprising at least one shielded anode and at least one shielded cathode, at least one second section comprising a connecting device for physically and electrically connecting said bipolar shielded lead to said stimulating device, and a third section physically and electrically connecting said first section and said second section, said third section comprising a device for conducting a stimulating current discharge generated by said stimulating device between said first section and said second section.

These and other objects are attained in the present invention which also provides a method for use with cardiomyoplasty of stimulating tissue comprising:
  contacting a paraneural stimulating lead with tissue to be stimulated;

connecting said paraneural stimulating lead to a stimulating device;
inducing said stimulating device to generate a stimulating current discharge;
transferring said stimulating current discharge to said tissue through said paraneural stimulating lead;
wherein said paraneural stimulating lead comprises a bipolar shielded lead further comprising at least one shielded anode and at least one shielded cathode, wherein the shielding of said shielded anode and said shielded cathode restricts the direction of flow of a stimulating current discharge so that said stimulating current discharge generated by said stimulating device flows unidirectionally into said tissue, said bipolar shielded lead further comprising a connecting device capable of physically and electrically connecting said bipolar shielded lead to said stimulating device, said bipolar shielded lead further comprising a device for electrically conducting said stimulating current discharge between said connecting device and said shielded anode and said shielded cathode.

The special or unique features of the paraneural stimulating lead of the present invention include several improved operational effects: reduction in the contact area between stimulated tissue and the stimulating lead; more precisely controlled direction of the stimulation; and reduction in the number of leads that need to be implanted from two to one plus elimination of a three-way adaptor and connections. The benefits of these results for the cardiomyoplasty procedure and patient include: shortened surgery time (reduction of lead implantation time); reduced sites for complications (elimination of one lead, one bulky adaptor and multiple connections); reduced costs of materials; increased battery life; extended time to stimulator replacement; and reduced costs for maintenance of the patient who has had cardiomyoplasty.

BRIEF DESCRIPTION OF THE DRAWINGS

FIG. 5A is an elevational, partially diagrammatic view of the negative (cathodic) dual screw-in type stimulating lead system in use in conjunction with a positive (anodic) intramuscular stimulating lead, implanted in a latissimus dorsi muscle flap;

FIG. 5B is an enlarged sectional view of the insertion of a screw-in type electrode within a latissimus dorsi muscle flap along the line 5B—5B of FIG. 5A;

FIG. 6A is a top plan view of the paraneural stimulating lead of the present invention;

FIG. 6B is a perspective enlarged view of the bipolar connector of FIG. 6A;

DESCRIPTION OF THE PREFERRED EMBODIMENTS

According to the present invention, a paraneural stimulating lead is provided for use in conjunction with the surgical procedure known as cardiomyoplasty.

To the extent necessary for a full understanding of the present invention, the teachings of U.S. Pat. No. 4,791,911 are hereby incorporated herein by reference.

In order to understand the present invention, it is necessary to be very familiar with the stimulating leads currently used in the cardiomyoplasty procedure. Therefore, the following discussion of FIGS. 1 through 4 will provide a review of those leads which have been utilized in the cardiomyoplasty procedure.

Figure 1:
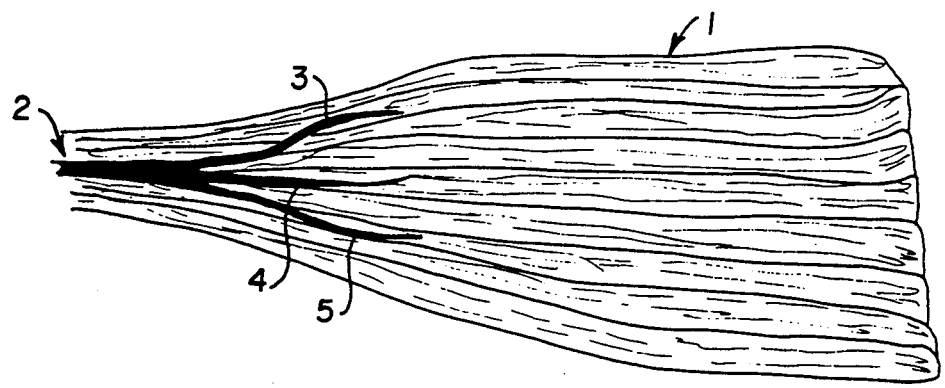
FIG. 1 is an elevational, partially diagrammatic view of the latissimus dorsi muscle flap showing the position of the neurovascular bundle and nerve branching.

Referring now to FIG. 1, the latissimus dorsi autograft or muscle flap 1 is shown. The nerve or neural trunk 2 branches into the three main nerve branches 3, 4, and 5. Although only the nerve branching is shown in FIG. 1, the major artery and vein serving the muscle flap, branch in a similar fashion from the trunk of the neural vascular bundle. Nerve branches 3, 4, and 5 continue branching and eventually permeate the whole of muscle flap 1.

Figure 2:
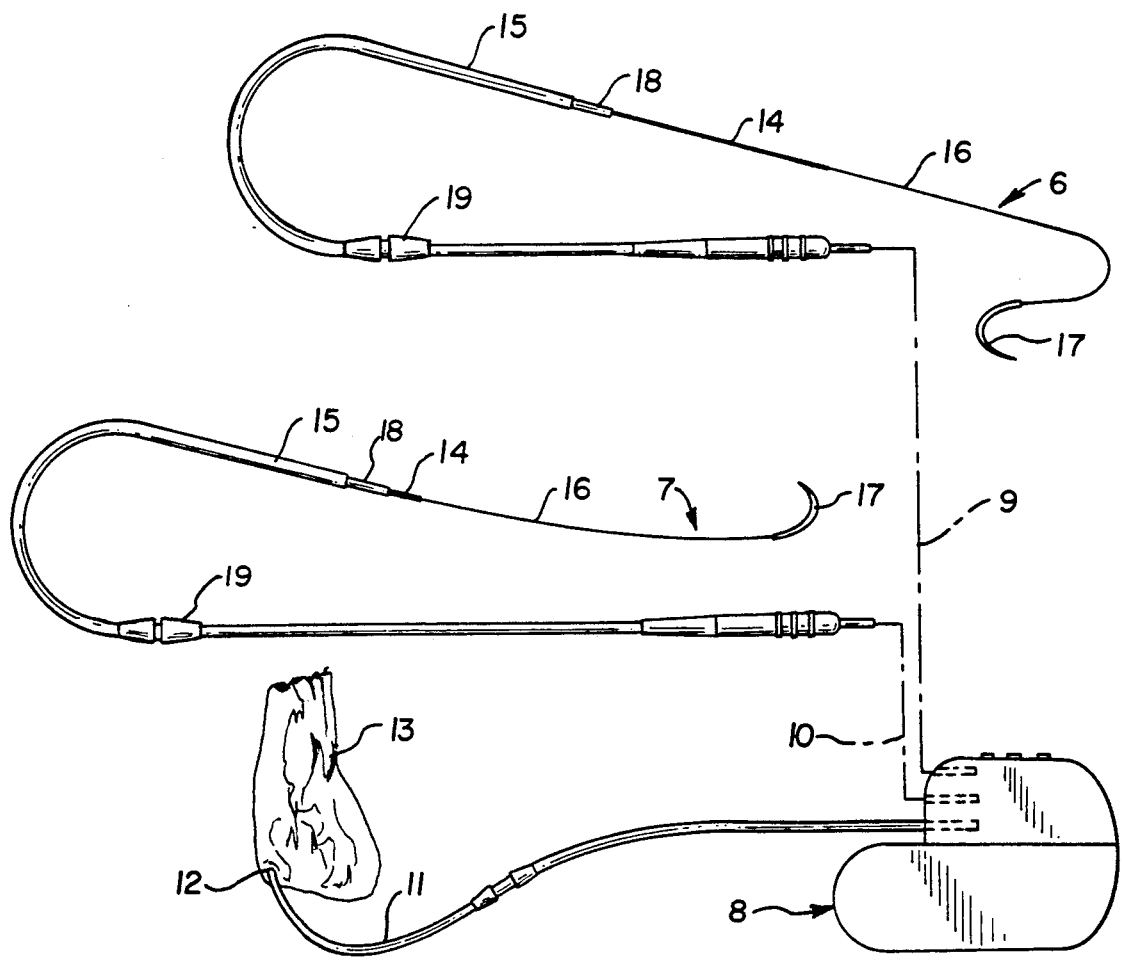
FIG. 2 is an elevational, partially diagrammatic view of the positive (anodic) and the negative (cathodic) leads of an intramuscular stimulating lead system.

FIG. 2 discloses an elevational, partially diagrammatic view of a positive (anodic) lead 6 and a negative (cathodic) lead 7 of the intramuscular stimulating lead system. The intramuscular stimulating lead system comprises an intramuscular anode lead 6 and an intramuscular cathode lead 7, the opposite ends of which are subsequently connected to cardio-muscle stimulator 8 as indicated by dotted lines 9, 10, which may include a specially designed dual unipolar to bipolar adaptor connector (not shown). Also shown is separate sensing lead 11 which is associated with a cardiac sensor 12, not shown, which senses the intrinsic electric signals of heart 13 and which, in turn, enables cardio-muscle stimulator 8 to provide its output signal in synchrony with the beating of heart 13.

Intramuscular anode lead 6 and intramuscular cathode lead 7 are identical, thus, the description of the cathode lead will also suffice as the description of the anode lead.

Intramuscular cathode lead 7 comprises a unipolar/unshielded flexible coil wire electrode 14 which is typically comprised of platinum-iridium, contained in moveable insulating sheath 15. The distal portion of intramuscular cathode lead 7 ends in a non-absorbable suture material 16 with a curved insertion needle 17 which permits lead insertion into muscle flap 1.

Once electrode 14 is properly placed in muscle flap 1, insulating sheath 15 is moved forward until its distal end 18 reaches the entrance site of electrode 14 into muscle flap 1. At this point, both suture material 16 and the distal end 18 are secured to muscle flap 1. Additionally, many electrodes currently used are provided with an anchoring sleeve 19 which may be anchored at any suitable portion in the body to further assist in holding the insulating sheath 15 in place.

Figure 3A:
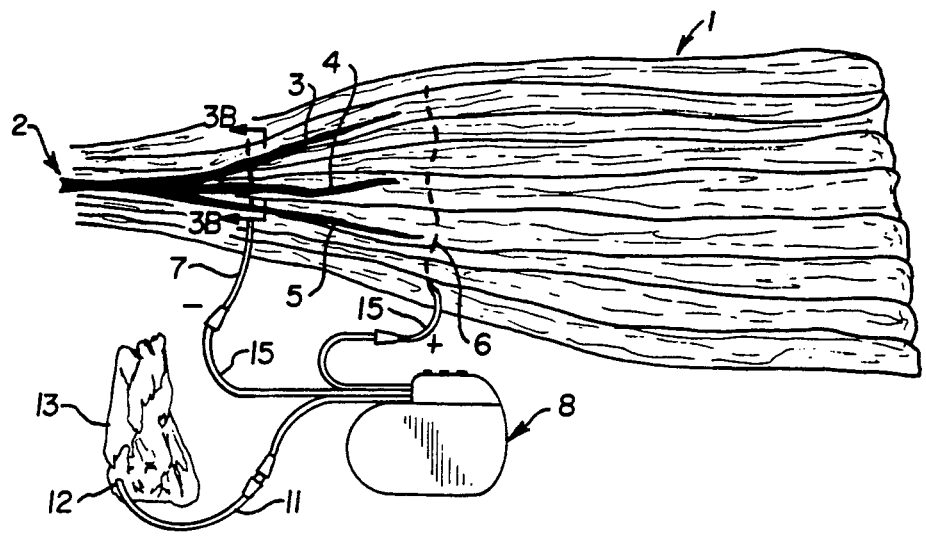
FIG. 3A is an elevational, partially diagrammatic view of the negative (cathodic) and the positive (anodic) leads of an intramuscular lead system implanted in a latissimus dorsi muscle flap.

FIG. 3A depicts the intramuscular stimulating lead system of the prior art stimulating muscle flap 1.

Figure 3B:
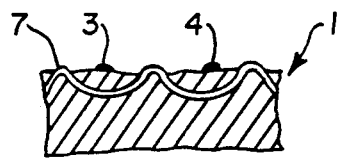
FIG. 3B is an enlarged sectional view of the insertion of an intramuscular electrode within a muscle flap, along the line 3B—3B of FIG. 3A.

Muscle flap 1 is shown with intramuscular anode lead 6 and intramuscular cathode lead 7 shown inserted in muscle flap 1, spaced approximately 5-10 cm. apart, near main nerve branches 3, 4, and 5 of muscle flap 1. Slideable insulating sheath 15 of both intramuscular anode lead 6 and intramuscular cathode lead 7 has been moved forward and sutured to muscle flap 1. Intramuscular anode lead 6 and intramuscular cathode lead 7 are shown connected to cardio-muscle stimulator 8. FIG. 3B is an enlarged, sectional view along the line 3B—3B of FIG. 3A showing the path of insertion of the electrode of intramuscular cathode lead 7 through muscle flap 1. The path of the electrode of intramuscular anode lead 6 is identical to the path of the electrode of intramuscular cathode lead 7. A cardiac sensor 12 (not shown) senses the intrinsic electric signals of heart 13, and the sensor transfers its signal via separate sensor lead 11 to cardio-muscle stimulator 8, which in turn generates a pulsed signal which transfers through intramuscular cathode lead 7, returning through intramuscular anode lead 6, and in so doing, causing muscle flap 1 to contract in synchrony with heart 13.

Figure 4:
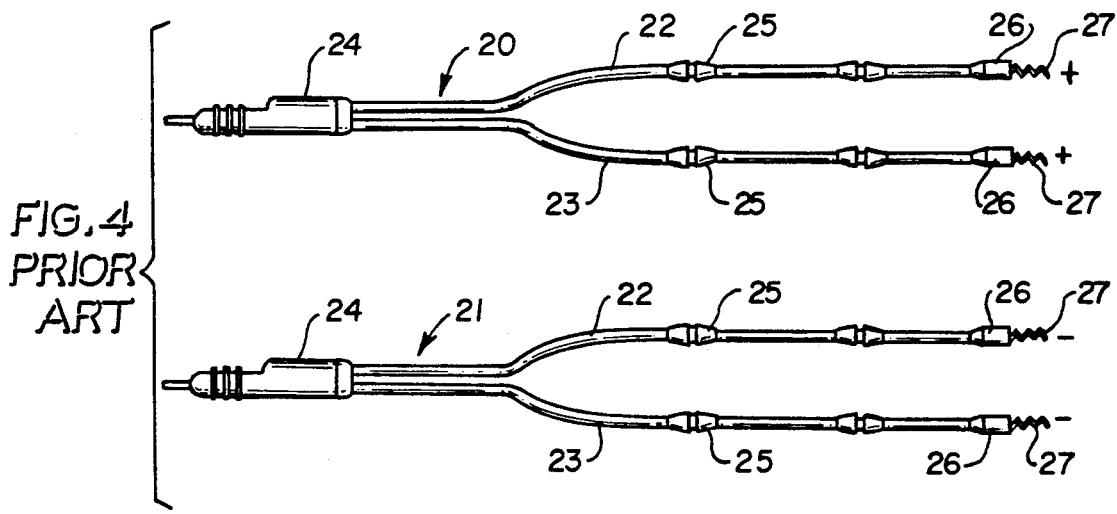
FIG. 4 is an elevational, partially diagrammatic view of the positive (anodic) and the negative (cathodic) leads of a dual screw-in type stimulating lead system.

FIG. 4 depicts a pair of dual screw-in type stimulating leads of the prior art, comprising dual screw-in type anode lead 20 and dual screw-in type cathode lead 21. These leads are dual unipolar/unshielded leads. An example of such a lead is Medtronic ® Model SP5537.

The dual screw-in type cathode lead 21 and the dual screw-in type anode lead 20 are identical. Therefore, the description of cathode lead 21 will also serve to describe the anode lead 20.

Dual screw-in type cathode lead 21 consists of two separate lead bodies 22 and 23 originating from one connector 24. Typically, one or more anchoring sleeves 25 assist in holding the stimulating lead in a fixed position in the body. Dual screw-in cathode lead 21 further comprises an electrode tip 26 which contains two grooves, not shown, in which the forks of an insertion tool, not shown, can be placed. The lead body is inserted into the slit of the tool shaft and rotated, typically 2.5 turns. Screwing the lead into muscle flap 1 will release these turns, fixing electrode element 27 into muscle flap 1. This procedure is repeated for each electrode element.

FIG. 5A depicts the stimulation of muscle flap 1 with the dual screw-in type stimulating lead system of the prior art, showing the use of dual screw-in type cathode lead 21 in use, in conjunction with an intramuscular anode lead 6, although those skilled in the art will realize that the anode could alternatively comprise dual screw-in type anode lead 20 as well. Muscle flap 1 is shown with dual screw-in cathode lead 21 and intramuscular anode lead 6 shown inserted in muscle flap 1, spaced approximately 6-12 cm. apart, near main nerve branches 3, 4, and 5 of muscle flap 1. FIG. 5B is an enlarged, sectional view along the line 5B—5B of FIG. 5A, showing the insertion of a screw-in type electrode element 27 inserted into muscle flap 1. Slideable insulating sheath 15 of the intramuscular anode lead 6 has been moved forward and sutured to muscle flap 1. Dual screw-in type cathode lead 21 and intramuscular anode lead 6 are connected to cardio-muscle stimulator 8 through a dual barrel adaptor (not shown). A cardiac sensor 12, (not shown), senses the systolic contraction of heart 13, and the sensor transfers its signal via sensor lead 11 to cardio-muscle stimulator 8, which, in turn, generates a pulsed signal through dual screw-in type muscular cathode lead 21, which returns through intramuscular anode lead 6, causing muscle flap 1 to contract in synchrony with heart 13.

Figure 7:
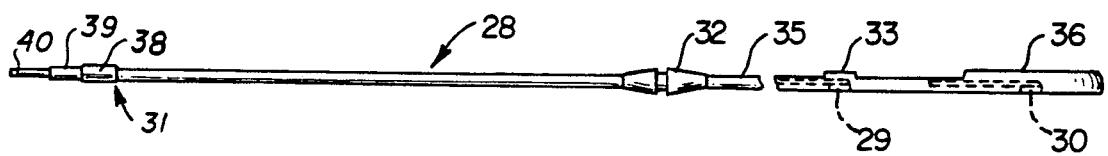
FIG. 7 is a side elevational view of the paraneural stimulating lead of the present invention.
Figure 8:
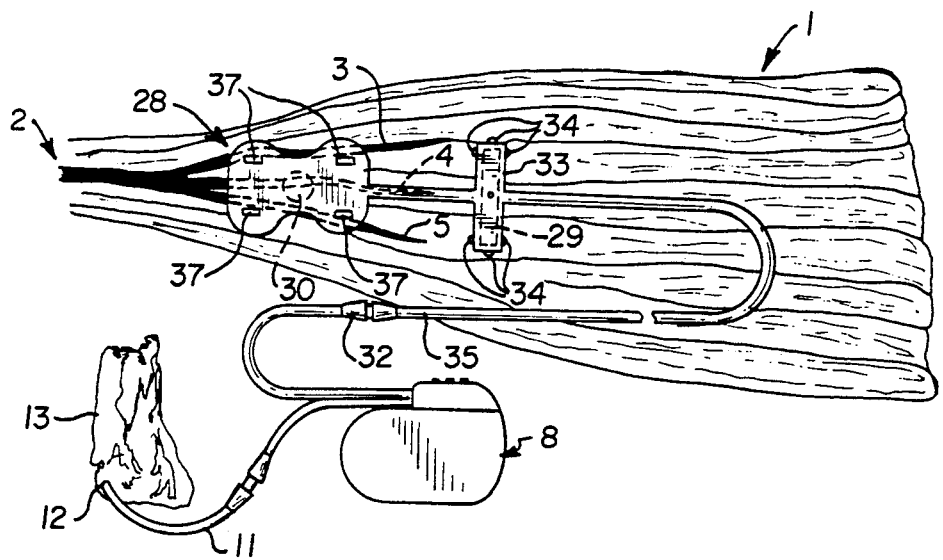
FIG. 8 is an elevational, partially diagrammatic view of the paraneural stimulating lead of the present invention implanted on a latissimus dorsi muscle flap.

FIGS. 6-8 disclose the advance of the present invention over the prior art. FIG. 6A discloses a top plan view of the paraneural stimulating lead 28 of the present invention. First, it is to be noted that the lead 28 is of a total length which may vary according to needs, and is bipolar, having both an anode 29 and a cathode 30 in a single lead, as shown in phantom in FIG. 6A. While depicted as having a single anode and a single cathode in FIG. 6A, it is to be understood that more than one anode and/or more than one cathode can be incorporated in the paraneural lead of the present invention. Further, it is to be understood that while the following discussion is directed to the use of the paraneural stimulating lead in the cardiomyoplasty surgical procedure, the lead of the present invention is suitable for use in a much wider variety of surgical procedures and/or wherever similar stimulation of tissue is desired, provided the tissue is susceptible to such stimulation. Paraneural stimulating lead 28 further comprises bipolar connector 31 and, optionally, one or more anchoring sleeves 32.

FIG. 6B is an enlarged perspective view of bipolar connector 31, comprising a positive or anode connector 38, and a negative or cathode connector 40, having been interposed between an insulating layer 39. Such connectors are known in the art as a means for providing both a positive and negative connection in one unit.

However, unlike bipolar leads of the prior art, the paraneural lead of the present invention is: shielded; has an elongated (approximately 4 cm. long by 2 mm. wide) anode 29 to provide for a better current distribution over the main nerve branches; and has a cathode 30 (approximately 3 mm in diameter) that is oriented spatially to face the nerve at the neurovascular bundle of the muscle flap which is to be stimulated, which further provides for a nearly point discharge of current (to achieve maximum current density over the nerve to be stimulated). The shieldings, 33 and 36, are also specifically designed for ease of attachment to the muscle flap 1 and may be comprised of silicon rubber, polyurethene or any material suitable for use as an electrically insulating material for a medical lead. Additionally, unlike neural stimulating leads of the prior art, the paraneural lead of the present invention does not require dissection of the nerve to be stimulated from the surrounding tissues.

Anode 29, shown in phantom in FIG. 6A, is surrounded by an insulating shielding 33 on all sides except for the side of the surface which faces muscle flap 1 when paraneural lead 28 is attached to muscle flap 1 thus providing a single or uni-directional current receiving path. The shielding 33 prevents dispersion of current in any direction except toward and into muscle flap 1. In a preferred embodiment of the present invention, anode insulating shielding 33 is further comprised with points of attachment 34. These points of attachment may be of any suitable design as is practiced in the art, which will permit easy, efficient, reliable attachment of insulating shielding 33 to muscle flap 1. Examples include but are not limited to barb type attachments, screw-in type attachments or holes/spaces which will permit suturing of insulating shielding 33 to muscle flap 1. Suturing holes are the preferred embodiment.

Anode 29 is also elongated in a direction perpendicular from the lead body 35. This elongation permits the current flow from cathode 30 to more or less follow the path of main nerve branches 3, 4, and 5 as it travels towards anode 29, providing a more efficient stimulation of muscle flap 1.

Cathode 30, which is shown in phantom in FIG. 6A, is surrounded by an insulating shielding 36 on all sides except for the side which faces muscle flap 1 when paraneural lead 28 is attached to muscle flap 1. The shielding 36 prevents discharge of current in any direction except into the nerve path at the neurovascular bundle of the muscle flap 1. In a preferred embodiment of the present invention, cathode insulating shielding 36 is further comprised of points of attachment 37. These points of attachment may be of any suitable design as is practiced in the art, which will permit easy, efficient, reliable attachment of insulating shielding 36 to muscle flap 1. Examples include but are not limited to barb type attachments, screw-in type attachments or holes/spaces which will permit suturing of insulating shielding 36 to muscle flap 1. Suturing holes are the preferred embodiment. Further, in a preferred embodiment, insulating shielding 36 is designed in a circular, daisy, rectangular or a "four-leafed clover" design, as depicted in FIG. 6A, to permit an easier, more stable attachment of the insulating material 36 to muscle flap 1.

Also, in a preferred embodiment and unlike endocardial bipolar pacing leads of the prior art, cathode 30 is designed such that this discharge directly faces muscle flap 1 when paraneural stimulating lead 28 is attached to muscle flap 1. This means that cathode 30 discharges at approximately a right angle from lead body 35, downward into the muscle flap 1.

Cathode 30 is further preferred to discharge in as nearly a point charge as possible to permit maximum current density over the nerve trunk 2 and/or main nerve branches 3, 4, and 5 of muscle flap 1. This in turn means that due to the increase in current density over the nerve trunk and main nerve branches of muscle flap 1, less current is needed to stimulate muscle flap 1, resulting in a reduced possibility of long-term electrical injury to the nerve structure and a much longer battery life in cardio-muscle stimulator 8.

FIG. 7 discloses a side elevational view of the paraneural stimulating lead 28 of the present invention. Cathode 30 and anode 29 are shown in phantom. Connector 31 is the same as that depicted in FIG. 6B.

FIG. 8 depicts the use of the bipolar/shielded paraneural stimulating lead system of the present invention. Muscle flap 1 is shown with paraneural lead 28, including anode 29 and cathode 30 (shown in phantom) attached to muscle flap 1 via sutures at points of attachment 37 and 34, with cathode 30 and anode 29 spaced approximately 3-10 cm. apart, near the nerve trunk 2 and main nerve branches 3, 4, and 5 of muscle flap 1. Fixation is accomplished by placing the distal tip, (negative) cathode 30 near the main trunk 2 and/or branches 3, 4, and 5 of the thoracodorsal nerve, care being taken not to disturb the thin layers of protective tissue covering the bundle, and placing two to three sutures from the shield to the muscular fibers, radially at either side. The proximal (positive) anode 29 is then fixed in the same manner, below the branching site of the nerve, at a position where the best fiber recruitment for muscular contraction can be achieved. Cathode 30 and anode 29 are shown connected via bipolar lead body 35 to cardiomuscle stimulator 8. A cardiac sensor, 12, (not shown), senses the systolic contraction of heart 13, and the sensor transfers its signal via sensor lead 11 to cardio-muscle stimulator 8, which in turn generates a pulsed signal through cathode 30, which returns through anode 29, causing muscle flap 1 to contract in synchrony with heart 13.

EXPERIMENTAL RESULTS

A paraneural stimulating lead was implanted in one patient on an experimental basis. The lead contributed to the successful augmentation of the patient's overall cardiac function.

Experimental testing of the paraneural stimulating lead in animals has demonstrated that the paraneural stimulating lead can be successfully used in the cardiomyoplasty procedure to continuously stimulate the muscle flap for prolonged periods. Successful use of the paraneural lead is defined to mean that either the paraneural lead sufficiently, measurably stimulated the muscle flap while functioning in the animal, and/or that when the animal was sacrificed, an autopsy revealed that the muscle flap had retained its viability.

Further the energy requirements for stimulation threshold of muscle flap were, on the average, less for the paraneural lead than the Medtronic ® Model SP5528 intramuscular lead. Here the threshold for stimulation is defined as the minimum energy supplied to the electrode to cause the muscle flap to twitch. Both of these leads, the paraneural lead and the Medtronic ® Intamuscular Stimulating Lead were made of a comparable platinum-iridium alloy. It is believed that the paraneural stimulating lead is capable of stimulating the muscle flap with a lower level of stimulating electricity because the discharge of stimulating electricity is a nearly point discharge directly into the muscle flap at a point nearly directly above its main nerve and/or main nerve branches. In contrast, the intramuscular stimulating lead is not a point discharge system but discharges its electricity over the entire length of its electrode.

As previously indicated, the paraneural lead is secured to the surface of the muscle flap, while in contrast, the intramuscular lead is inserted into the muscle flap. While the insertion of the electrode of the intramuscular lead into the muscle flap would tend to place the electrode closer to the nerve and would thereby seem to be able to achieve stimulation with a lower threshold than that of the paraneural stimulating lead, this has been found experimentally not to be the case. It is believed that this is due in part to the fact that the intramuscular lead is not capable of a point discharge of electrical energy directly over the nerve itself, and due in part to the fact that it is not possible to place the intramuscular lead all that much closer to the nerve than the paraneural lead, without risking undesirable damage to the artery and vein which would ruin the muscle flap for purposes of the cardiomyoplasty.

When comparing the paraneural stimulating lead of the present invention to Medtronic ® Model SP5528, results indicate that, in addition to the more convenient and safe implanting process, the paraneural stimulating lead of the present invention has the following advantages: a) lower power usage than with the Medtronic ® SP5528 intramuscular lead system, which should result in an increased battery life in any given case. This means less damage to neural and muscular cells and the potential extension of battery life; and, therefore, extension of time span between cardio-muscle stimulator replacements and a corresponding reduction in the number of cardio-muscle stimulator replacement procedures over the life of the patient. To these, one more advantage is added for the benefit of the recipient: one lead and a bulky adaptor are eliminated, and with them the risk of (two) connections fastened with set screws, as another potential source of eventual malfunction as it happens in pacing and stimulation.

One of the limiting factors to the degree of success of cardiomyoplasties at this time is lack of availability of a suitable leads to accommodate the particular needs of the patient after cardiomyoplasty, a lead system should have the capacity for stimulating skeletal muscle to respond as heart muscle without unnecessary use of excess power for stimulation of tissue—(which can trigger damage to the skeletal muscle fibers which can reduce the beneficial effect of the cardiomyoplasty). It is also important that the lead be implantable with minimal risk of damage to vascular structures (e.g., with a leading needle), which would also negatively impact on the outcome of the cardiomyoplasty procedure. Thus, it is not only the individual procedure and patient that may benefit from the availability of a lead based on the concepts of this invention, but the field of cardiomyoplasty may be significantly advanced when an appropriate lead is available for routine use.

Having described the invention, it is to be understood that the invention is not limited to this precise device and method for using the same, and that changes may be made therein without departing from the scope of the present invention which is defined in the appended claims.

I claim:

1. A paraneural stimulating lead attached to stimulating means and which is spaced from a nerve of tissue to be stimulated, said paraneural lead comprising:
   at least one first section comprising a bipolar, shielded lead which is spaced from said nerve of the stimulated tissue further comprising at least one shielded anode and at least one shielded cathode;
   at least one second section comprising a connecting means for physically and electrically connecting said paraneural stimulating lead to said stimulating means;
   a third section physically and electrically connecting said first section and said second section, said third section comprising a means for conducting a stimulating current discharge generated by said stimulating means between said first section and said second section; and
   wherein the shielding of said shielded anode and said shielded cathode further comprises a means for attachment of said bipolar shielded lead to said tissue spaced from said nerve.

2. The paraneural stimulating lead of claim 1, wherein said stimulating means is a cardio-muscle stimulator and said paraneural stimulating lead is used for cardiac or circulatory augmentation including cardiomyoplasty.

3. The paraneural stimulating lead of claim 1, wherein said connecting means is a bipolar single unit connecting means providing both positive and negative connections in one unit.

4. The paraneural stimulating lead of claim 1 wherein said shielding further comprises a means for attachment of said bipolar shielded lead to a muscle flap.

5. The paraneural lead of claim 1, further comprising at least one anchoring sleeve positioned between said connecting means and said shielded anode and said shielded cathode.

6. A method of stimulating cardiac and non-cardiac tissue comprising:
   contacting a paraneural stimulating lead with tissue to be stimulated;
   connecting said paraneural stimulating lead to a stimulating means;
   inducing said stimulating means to generate a stimulating current discharge;
   transferring said stimulating current discharge to said tissue through said paraneural stimulating lead;
   wherein said paraneural stimulating lead comprises at least one first section comprising a bipolar, shielded lead further comprising at least one shielded anode and at least one shielded cathode, at least one second section comprising a connecting means for physically and electrically connecting said bipolar shielded lead to said stimulating means, and a third section physically and electrically connecting said first section and said second section, said third section comprising a means for conducting a stimulating current discharge generated by said stimulating means between said first section and said second section.

7. A method for use with cardiomyoplasty of stimulating tissue comprising:
   contacting a paraneural stimulating lead with tissue to be stimulated;
   connecting said paraneural stimulating lead to a stimulating means;
   inducing said stimulating means to generate a stimulating current discharge;
   transferring said stimulating current discharge to said tissue through said paraneural stimulating lead;
   wherein said paraneural stimulating lead comprises a bipolar shielded lead further comprising at least one shielded anode and at least one shielded cathode, wherein the shielding of said shielded anode and said shielded cathode restricts the direction of flow of a stimulating current discharge so that said stimulating current discharge generated by said stimulating means flows unidirectionally into said tissue, said bipolar shielded lead further comprising a connecting means capable of physically and electrically connecting said bipolar shielded lead to said stimulating means, said bipolar shielded lead further comprising a means for electrically conducting said stimulating current discharge between said connecting means and said shielded anode and said shielded cathode.

8. The method of stimulating tissue of claim 6, wherein said contacting of said lead with said tissue is at the surface of said tissue spaced from the nerve of said tissue to be stimulated.

9. The method of stimulating tissue of claim 8, wherein said lead is attached to said tissue surface.

10. The method of stimulating tissue of claim 7, wherein said contacting of said lead with said tissue is at the surface of said tissue spaced from the nerve of said tissue to be stimulated.

11. The method of stimulating tissue of claim 10, wherein said lead is attached to said tissue surface by said shield lead connecting means.

12. A method of stimulating tissue, for use with cardiac or circulatory augmentation including cardiomyoplasty, comprising:
   contacting a paraneural stimulating lead with tissue to be stimulated;
   connecting said paraneural stimulating lead to a stimulating means;
   inducing said stimulating means to generate a stimulating current discharge;

transferring said stimulating current discharge to said tissue through said paraneural stimulating lead;

wherein said paraneural stimulating lead comprises a bipolar shielded lead further comprising at least one shielded anode and at least one shielded cathode, wherein the shielding of said shielded anode and said shielded cathode restricts the direction of flow of a stimulating current discharge so that said stimulating means flows unidirectionally into said tissue, sad bipolar shielded lead further comprising a connecting means capable of physically and electrically connecting said bipolar shielded lead to said stimulating means, said bipolar shielded lead further comprising a means for electrically conducting said stimulating current discharge between said connecting means and said shielded anode and said shielded cathode.

13. The method of stimulating tissue of claim 12, wherein said contacting of said lead with said tissue is at the surface of said tissue spaced from the nerve of said tissue to be stimulated.

14. The method of stimulating tissue of claim 13, wherein said lead is attached to said tissue surface by said shield lead connecting means.

* * * * *